United States Patent
Ionasec

(10) Patent No.: US 11,056,228 B2
(45) Date of Patent: Jul. 6, 2021

(54) METHOD AND SYSTEM FOR EVALUATING MEDICAL EXAMINATION RESULTS OF A PATIENT, COMPUTER PROGRAM AND ELECTRONICALLY READABLE STORAGE MEDIUM

(71) Applicant: Siemens Healthcare GmbH, Erlangen (DE)

(72) Inventor: Razvan Ionasec, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 227 days.

(21) Appl. No.: 16/243,273

(22) Filed: Jan. 9, 2019

(65) Prior Publication Data
US 2019/0221304 A1 Jul. 18, 2019

(30) Foreign Application Priority Data
Jan. 12, 2018 (EP) .................................... 18151452

(51) Int. Cl.
*G06T 7/00* (2017.01)
*G16H 30/40* (2018.01)
(Continued)

(52) U.S. Cl.
CPC ............. *G16H 30/40* (2018.01); *G06F 40/20* (2020.01); *G06K 9/6256* (2013.01); *G06T 7/0012* (2013.01); *G16H 15/00* (2018.01); *G16H 50/20* (2018.01); *G06K 2209/05* (2013.01); *G06T 2207/20081* (2013.01); *G06T 2207/20084* (2013.01)

(58) Field of Classification Search
CPC .............................. G16H 30/40; G16H 15/00
See application file for complete search history.

(56) References Cited

U.S. PATENT DOCUMENTS

| 8,705,825 B2 * | 4/2014 | Olson | G16H 30/20 |
| | | | 382/128 |
| 9,764,162 B1 * | 9/2017 | Willcut | G06T 7/0012 |
| 2008/0201280 A1 * | 8/2008 | Martin | G06Q 50/24 |
| | | | 706/12 |

OTHER PUBLICATIONS

European Office Action dated Jul. 28, 2020.
(Continued)

*Primary Examiner* — Tuan H Nguyen
(74) *Attorney, Agent, or Firm* — Harness, Dickey & Pierce, P.L.C.

(57) ABSTRACT

A method is for evaluating medical examination results of a patient. The method includes providing a medical ontology including multiple medical concepts occurring in image data sets and examination reports of patients; analysing the at least one image data set using at least one first analysis algorithm, the at least one first analysis algorithm being an artificial intelligence algorithm, for detection of medical concepts of the medical ontology, and marking the medical concepts detected in a result data structure referring to the medical ontology; analysing the at least one examination report using at least one second analysis algorithm, the at least one second analysis algorithm being a natural language processing algorithm, for detection of other medical concepts of the medical ontology, and marking the other medical concepts detected in the result data structure; and providing the result data structure to at least one evaluation application processing medical concepts.

20 Claims, 2 Drawing Sheets

(51) Int. Cl.
*G16H 15/00* (2018.01)
*G16H 50/20* (2018.01)
*G06F 40/20* (2020.01)
*G06K 9/62* (2006.01)

(56) References Cited

OTHER PUBLICATIONS

Pons, Ewoud et al.: "Natural Language Processing in Radiology: A Systematic Review"; in: Radiology; vol. 279; No. 2; pp. 329-343; 2016; doi: 10.1148/radiol.16142770.
European Search Report Patent Application No. 18151452.2 dated Jun. 6, 2018.

* cited by examiner

METHOD AND SYSTEM FOR EVALUATING MEDICAL EXAMINATION RESULTS OF A PATIENT, COMPUTER PROGRAM AND ELECTRONICALLY READABLE STORAGE MEDIUM

PRIORITY STATEMENT

The present application hereby claims priority under 35 U.S.C. § 119 to European patent application number EP 18151452.2 filed Jan. 12, 2018, the entire contents of which are hereby incorporated herein by reference.

FIELD

Embodiments of the invention generally relate to a method and an evaluation system for evaluating medical examination results of a patient, a computer program and an electronically readable storage medium.

BACKGROUND

Medical imaging, i.e. radiology, has proven to be a powerful tool for diagnosing and treating patients. Different modalities may be used for different medical tasks, wherein in particular x-ray imaging (comprising CT), magnetic resonance imaging and ultrasound imaging have been established as common radiological modalities. In different medical facilities, for example hospitals or radiological doctor's offices, patients can undergo radiological examinations, leading to image data sets of the patient.

However, radiological examination reports are the final product of the radiologist's work. Such reports are usually manually compiled and formulated in natural language by the radiologist himself. Radiological examination reports and radiological image data sets comprise a large portion of the digital medical content available today that may potentially be a valuable source of information for clinical care, clinical research, clinical management, and other healthcare related processes.

Although radiological examination reports may be stored electronically, for example in electronic health records of a patient, their formulation in natural language poses a problem, since they lack a known structure and are highly variable among the radiologists. The lack of structure impedes extracting and reliably transferring information from large numbers of examination reports, thus prohibiting the development and implementation of large scale data-driven applications.

Medical images may also be stored electronically and exhibit a much higher degree of standardization and reproducibility than radiological reports, so that based in image data sets rapid scaling of data-driven applications would be possible. However, the reliable extraction of high level structured information from images is extremely complex and can only be accomplished by humans or with human assistance.

SUMMARY

The inventors have discovered that a lack of availability of large scale structured radiological data has been limiting the types and numbers of data-driven applications available today. Hence, applications operational today are limited by the type of the information they can extract (e.g. CAD detection from images), are custom made for specific institutions/facilities or use specific handcrafted features, and, in general, lack robustness. Therefore, the use of such evaluation applications is not widespread and existing evaluation applications are mostly restricted in functionality and purpose.

An embodiment of the invention provides a foundation for the development and use of evaluation applications, rendering these more robust and providing a larger scope of applicability, in particular to large fields of radiology and medicine and/or large numbers of cases.

Embodiments of the invention provide a method, an evaluation system, a computer program and an electronically readable storage medium. Preferred embodiments are described by the claims.

An embodiment of the invention is directed to an inventive method for evaluating medical examination results of a patient, the medical examination results comprising at least one image data set of the patient and at least one examination report written in natural language, the method, using a computing device, comprising:

providing a medical ontology comprising multiple medical concepts occurring in image data sets and examination reports of patients, analysing the at least one image data set using at least one first analysis algorithm, the first analysis algorithm being an artificial intelligence algorithm, for detection of medical concepts of the medical ontology and marking detected medical concepts in a result data structure referring to the medical ontology, analysing the at least one examination report using at least one second analysis algorithm, the second analysis algorithm being a natural language processing algorithm, for detection of medical concepts of the medical ontology and marking detected medical concepts in the result data structure, and providing the result data structure to at least one evaluation application processing medical concepts.

An embodiment of the invention is directed to an inventive method for evaluating medical examination results of a patient, the medical examination results including at least one image data set of the patient and at least one examination report written in natural language, the method, performed using a computing device, comprising:

providing a medical ontology including multiple medical concepts occurring in image data sets and examination reports of patients;

analysing the at least one image data set using at least one first analysis algorithm, the at least one first analysis algorithm being an artificial intelligence algorithm, for detection of medical concepts of the medical ontology, and marking the medical concepts detected in a result data structure referring to the medical ontology;

analysing the at least one examination report using at least one second analysis algorithm, the at least one second analysis algorithm being a natural language processing algorithm, for detection of other medical concepts of the medical ontology, and marking the other medical concepts detected in the result data structure; and providing the result data structure to at least one evaluation application processing medical concepts.

An embodiment of the evaluation system or its computing device, having a processor and a memory, may comprise a first concept detection unit or subsystem for extraction of structured information from image data sets, a second concept detection unit or subsystem for extraction of structured information from text, i.e. the examination reports, an output unit or subsystem for data representation in form of a result data structure relating to the medical ontology, and multiple application units/subsystems for specific evaluation applications.

An embodiment of the invention is directed to an evaluation system for evaluating medical examination results of a patient, the medical examination results including at least one image data set of the patient and at least one examination report written in natural language, the evaluation system comprising:

at least one processor configured to provide a medical ontology including multiple medical concepts occurring in image data sets and examination reports of patients, analyse the at least one image data set using at least one first analysis algorithm, the at least one first analysis algorithm being an artificial intelligence algorithm, for detection of medical concepts of the medical ontology, and marking the medical concepts detected in a result data structure referring to the medical ontology, analyse the at least one examination report using at least one second analysis algorithm, the at least one second analysis algorithm being a natural language processing algorithm, for detection of other medical concepts of the medical ontology, and marking the other medical concepts detected in the result data structure, and provide the result data structure to at least one evaluation application processing medical concepts.

A non-transitory computer program product according to an embodiment of the invention comprises a program including computer program segments configured to perform the steps of a method according to an embodiment of the invention when the computer program is executed in a computing device, in particular the computing device of an evaluation system according to an embodiment of the invention.

In an embodiment, the computer program may be stored on an electronically readable storage medium, which thus has electronic control information comprising a computer program according to an embodiment of the invention stored thereon, such that, when the electronically readable storage medium is used in a computing device, the computing device is controlled to perform a method according to the invention. The electronically readable storage medium may non-transitional, for example a CD ROM.

BRIEF DESCRIPTION OF THE DRAWINGS

Further details and advantages of the current invention can be seen from the following description of preferred embodiments taken in conjunction with the figures, in which.

DETAILED DESCRIPTION OF THE EXAMPLE EMBODIMENTS

Figure 1:
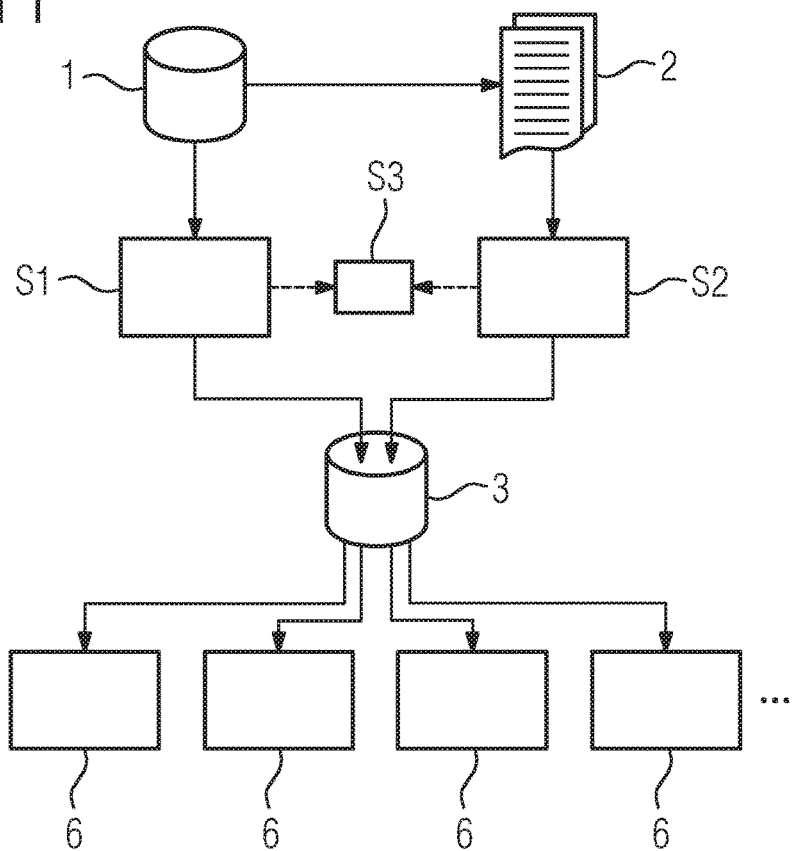
FIG. 1 shows a flow chart of a method according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

An embodiment of the invention is directed to a computer-implemented evaluation method for evaluating medical examination results of a patient, the medical examination results comprising at least one image data set of the patient and at least one examination report written in natural language, the method, using a computing device, comprising:

providing a medical ontology comprising multiple medical concepts occurring in image data sets and examination reports of patients, analysing the at least one image data set using at least one first analysis algorithm, the first analysis algorithm being an artificial intelligence algorithm, for detection of medical concepts of the medical ontology and marking detected medical concepts in a result data structure referring to the medical ontology, analysing the at least one examination report using at least one second analysis algorithm, the second analysis algorithm being a natural language processing algorithm, for detection of medical concepts of the medical ontology and marking detected medical concepts in the result data structure, and providing the result data structure to at least one evaluation application processing medical concepts.

Medical concepts describe, in particular in natural language, medical conditions relevant to the patient, in particular medical anomalies and medical characteristics of the patient, which do not have to be illnesses as such, but can also describe circumstances characteristic to the patient, for example non-malignant tissue abnormalities and the like. Examples for medical concepts comprise diseases of the vascular system, lung nodules, and calcipenia or other deficiencies, or, on a broader scale, examinations and/or findings in certain organs, for example lung, heart, liver, and the like. By using medical image data sets, thus radiological images, the method's main application is radiology, such that the medical ontology may also be termed a radiological concept ontology.

Embodiments of a computer-implemented evaluation method and system are thus proposed which extract structured information, i.e. the result data structure, from radiological examination reports in combination with radiological image data sets using analysis algorithms, in particular at least partly machine-learning based. The structured information is represented within a medical ontology, which can also be termed a radiological concept ontology, which preferably covers all or at least most medical fields affected by radiology. The result data structure may subsequently be used to enable multiple evaluation applications, in particular data-driven evaluation applications working on large amounts of data, in this case, for example, a database of result data structures. As will be further detailed below, applications may comprise radiological case interpretation assistance, billing, coding, compliance and legal liability, clinical trials and registries, clinical management and radiological report generation/post-processing.

In an embodiment, the input of the evaluation method/system comprises both of unstructured text, in form of radiological examination reports (including/extendible to electronic health records, historical records, other records such as pathology, lab reports, etc.) and image data sets, in form of radiological images (this includes any image modality, in particular x-ray, MR and/or ultrasound, historical acquisitions, multi-modal images, pathology images, invasive images, etc.). In particular, the whole (electronically) available medical history of the patient, in particular in an electronic health record (EHR, often also termed EMR—electronic medical record) can be used as input data for the evaluation. Preferably, however, the examination results comprise at least image data sets and their associated examination reports, wherein, in embodiments, also historical acquisitions can be considered.

Marking according to an embodiment of the current invention can comprise the binary activation of medical concepts detected in the image data sets and/or the examination reports. In particular, the result data structure may comprise a bit for each medical concept in the ontology. Using binary activation, the output of the evaluation method/system is represented by a binary activation list of predefined medical concepts from the medical ontology. Generally, the result data structure can be seen as a marked medical concept pattern.

This output can be easily used to enable a vast spectrum of applications that can be developed independently based on the medical ontology. Thus, the medical ontology can be seen as providing an interface for applications working with examination results. Since the result data structure and the medical ontology are clearly defined, the robustness of such applications is improved.

In particular, an embodiment of the evaluation system or its computing device, having a processor and a memory, may comprise a first concept detection unit or subsystem for extraction of structured information from image data sets, a second concept detection unit or subsystem for extraction of structured information from text, i.e. the examination reports, an output unit or subsystem for data representation in form of a result data structure relating to the medical ontology, and multiple application units/subsystems for specific evaluation applications.

In an especially preferred embodiment, the medical ontology is hierarchically structured, wherein multiple first and/or multiple second analysis algorithms are used, at least in part following the hierarchical structure, such that, on detection of a medical concept of a higher hierarchical level using a first or second analysis algorithm of the higher hierarchical level, at least one analysis algorithm of the next lower hierarchical level, if existent, is used to detect medical concepts of this next lower hierarchical level. Using a hierarchically structured ontology allows hierarchical running of respective detectors of the analysis algorithms. This, in turn, enables an efficient and flexible processing.

In particular, the number of processing steps can be reduced, since the hierarchical structure, being based on physical dependencies, allows skipping the detection of sub-concepts if a higher level medical concept as prerequisite is not present. Additionally, a hierarchical structure of the medical ontology allows flexibility regarding the subsequent evaluation applications, tailoring the analysis process to their needs. Preferably, the hierarchical structure is at least partly in at least one hierarchical level using anatomical features for distinction of medical concepts. For example, radiological examinations may be structured according to body sections and organs. Chest examinations at a higher level may include heart examinations, lung examinations, etc. as hierarchically subsequent medical concepts.

Preferably, the medical ontology is based on at least one predefined known ontology and/or at least one predefined denotation standard and/or a mapping from the medical ontology to at least one predefined known ontology and/or at least one predefined denotation standard is provided. Thus, while the medical ontology may, in principle, already use such known ontologies and/or standards, at least a mapping to these pre-known entities may be provided. This allows evaluation applications working on a certain structural basis, for example by allocating information and/or events to certain medical concepts contained in a predefined known ontology or denotation standard (often also called "lexicon"), to exploit the information of the data structure in a suitable manner.

Examples for such known, predefined ontologies/denotation standards include RadLex as a radiology-specific ontology, SNOMED (Systematized Nomenclature of Medicine), Gamuts, the National Cancer Institute Thesaurus, ICD (International Statistical Classification of Diseases and Related Health Problems), Medical Subject Headings (MeSH), and RADS (Reporting and Data Systems) for different anatomical features. The mapping functionality may be used by evaluation applications using the corresponding predefined ontology and/or denotation standard/lexicon.

Artificial intelligence is used for extraction of medical concepts from image data sets. Machine learning-based approaches have proven to overcome some of the problems in automatic image interpretation, allowing to determine valuable information from images, at least concerning general concepts, and as such providing a basis for a robust determination of the result data structure.

In a preferred embodiment, a convolutional neural network (CNN) is used as the at least one first analysis algorithm, in particular trained using deep learning techniques. CNNs have proven to be particularly suitable for image processing of medical image data sets, reliably recognizing features relating to medical concepts.

Preferably, training data sets are determined by applying the at least one second analysis algorithm to a training examination report associated with a training image data set, wherein the results of the second analysis algorithm at least partly form the ground truth for the training image data set. For a given training data set of radiological examination reports and image data sets, the second analysis algorithms for extraction of information from text may be used to generate labels in form of activated medical concepts by analysing an examination report associated with the image data set. All detected medical concepts are considered positive labels for the corresponding image data sets, while medical concepts that were not detected are considered negative labels. Further training information may be added by manual annotation of the image data sets to further improve the quality of the training data. Preferably, as already mentioned, deep learning techniques are applied while training first analysis algorithms.

If the at least one first analysis algorithm comprises a detector for each of the defined medical concepts, these detectors, in particular CNN detectors, are trained to detect the presence of the corresponding medical concept from a given input image data set. The training data set may be structured such that image data sets containing the medical concept, i.e. labelled positive, are used as positive examples, while the rest of the training data set is used as negative examples. Data pre-processing and training set augmentation techniques as known in the state of the art may be used within the training process.

Preferably, first analysis algorithms are provided for single medical concepts and/or groups of medical concepts of the hierarchically structured medical ontology, wherein, when training the first analysis algorithms, the training results for a hierarchically next higher medical concept are, at least partly, used as a starting point for training the at least one first analysis algorithm for the hierarchically lower, subordinate medical concepts in the respective tree. For efficiency, the analysis algorithms, in particular CNN, may be trained in a hierarchical process. For example, the first analysis algorithm training results for a "valvular disease" concept may be used as the initial algorithm parameters for training the first analysis algorithm for the subordinate "aortic valve disease" concept.

Preferably, analysing the examination reports using the second analysis algorithm comprises the steps of feature extraction and detection based on extracted features. Feature extraction may comprise a section separation function to divide the radiological examination reports into main sections, for example comprising imaging techniques, impression, patient history studies, etc., a sentence splitting function and a tokenization function to separate sentences and subsequently the words. Further, the feature extraction may comprise normalization to determine the lexical root, fix spelling mistakes, and resolve abbreviations. Multi-language support may also be provided. The feature extraction may further comprise syntactic analysis, semantic analysis based on existent lexicons (RadLex, SNOMED, etc.), and negation detection. The resultant information is used to create features subsequently used for medical concept detection.

Based on these features, for each medical concept or a group of medical concepts of the medical ontology, a detector in the second analysis algorithm or as second analysis algorithm may be employed to determine the presence of these medical concepts from a given radiological examination report. The second analysis algorithm may use a combination of rule-based and machine learning-based methods. In other words, at least one of the at least one second analysis algorithm may be at least partly rule-based and/or at least partly artificial intelligence-based. While the detection of some medical concepts may be straightforward given by the presence of certain words in the report, for more complex medical concepts, a machine learning-based system may be used. The training data sets for this approach are provided by manually annotating examination reports with specific labels from the medical ontology.

By analysing images as well as reports, the current invention provides the possibility of a plausibility check and/or broadening the basis for further analysis. While this can, in particular, be exploited by the evaluation applications as described below, the invention also allows, for example, a plausibility check while aggregating the results of the first and second analysis algorithms.

In a respective embodiment, the detection results of both analysis algorithms may be compared, wherein, when at least one medical concept, in particular of a relevancy group of medical concepts, found in the image data set is not found in the examination report, a notification regarding this medical concept is output. In this manner, for example, a re-assessment of the image data set can be triggered.

In concrete embodiments, at least one evaluation application is chosen from the group including an interpretation assistance application, a billing and/or coding and/or quality assessment and/or legal assessment application, a clinical trial and/or clinical management application, and a radiological report assistance application. Other applications are, of course, also conceivable.

In a first preferred example embodiment, the interpretation assistance application is a propagation application, which propagates critical findings detected by rule-based evaluation of the result data structure in a computer system of a medical facility, and/or a related cases finding assistant, which compares a result data structure of a current patient with result data structures of other patients stored in a database. In particular, medical concepts may be weighed during comparison. For example, a simple rule-based algorithm can be employed based on the medical ontology to detect critical findings and propagate alerts within the computer system, for example to information systems of a healthcare information technology system.

If, for example, a "lung nodules" concept is detected, which does not represent a critical finding, no propagation is required. If, however, a "pneumothorax" concept has been detected, which represents a critical finding, the finding is propagated, for example by triggering an alarm signal regarding the patient to other subsystems of the computer system. Additionally and/or alternatively, based on the retrospectively structured data of the inventive evaluation system, related similar cases can be retrieved on the basis of similar patterns of marked medical concepts of the medical ontology. Each medical concept may be associated with a weight to further improve the performance of the similar case retrieval function of the related cases finding assistant.

Preferably, the billing and/or coding application may map the result data structure to a corresponding billing code, in particular according to a billing standard. The billing standard may, for example, be ICD-10 and/or CPT (Current Procedural Terminology). The mapping to the billing code may be rule-based and/or machine learning-based. In this manner, automated billing may be realized. Further preferably, the legal assessment application may compute a legal hazard potential score from the result data structure using a database with reference values based on other cases.

In other example preferred embodiments, the clinical trial application retrieves cases fitting a requirement definition for a prospective and/or historical study based on their result data structures and/or the clinical management application evaluates the result data structure with respect to predetermined clinical guidelines to generate recommendations on further procedures regarding the patient. The evaluation system may be used for retrospective cohort generation as well as for identification of prospective cases for prospective, that is, ongoing clinical studies. Specific inclusion criteria may be defined using the medical ontology representation. Based on the marked medical concepts pattern for a specific case/patient and the defined inclusion criteria, it can be determined if the specific case is relevant for any of the active clinical trials, registries, or any other studies and/or cohorts.

Regarding clinical management, the evaluation system may be used to generate recommendations for subsequent examinations and clinical management in general. A specific medical ontology pattern, for example associated with inconclusive results, may be defined to provide a recommendation for further examinations. If, for example, an enlarged heart was found in x-ray exams without a concrete diagnosis, a certain MR examination may be proposed for clarification. In general, marked medical concept patterns may be used in the recommendation of follow-up examinations, in particular according to facility guidelines and/or standards, such as the LUNG-RADS. In an example, a specific LUNG-RADS class may be detected from the marked medical concepts pattern, which may lead to recommendations for subsequent examinations.

In especially preferred example embodiments, the radiological report assistance application generates drafts for examination reports based on result data structures of previous examination results and/or current image data sets and/or offers real time and/or post-processing assistance based on these result data structures. The evaluation system may thus, for example, be used in an interactive mode, where the result data structure is being updated while the examination report is generated. In turn, auto-filling functions of parts of the examination report, formulation recommendation functions, in particular in regard of predefined known ontologies and/or denotation standards/lexica, or inference functions proposing further medical concepts may be provided. Such functions may also refer to previous examinations, i.e. sets of associated image data sets and examination reports, or be used for post-processing of examination reports.

The medical ontology may further be used to enable multi-language support for translation or generation of examination reports, for example, if a translation of radiological examination reports from one language into another is required. This facilitates patients receiving healthcare service in multiple countries and enables drive-by-globalization and/or practices like healthcare tourism. Therefore, the medical ontology may be associated with at least one dictionary for multiple languages, such that the translation of the medical concepts into other languages is enabled.

A non-transitory computer program product according to an embodiment of the invention comprises a program including computer program segments configured to perform the steps of a method according to an embodiment of the invention when the computer program is executed in a computing device, in particular the computing device of an evaluation system according to an embodiment of the invention.

In an embodiment, the computer program may be stored on an electronically readable storage medium, which thus has electronic control information comprising a computer program according to an embodiment of the invention stored thereon, such that, when the electronically readable storage medium is used in a computing device, the computing device is controlled to perform a method according to the invention. The electronically readable storage medium may non-transitional, for example a CD ROM.

FIG. 1 shows a flow chart of an embodiment of a method according to the invention. As in principle known in the state of the art, a medical image acquisition device is used to acquire an image data set 1 of a patient. Using, for example, a workstation, a radiologist or other medical personal views the image data set 1 and sums up his findings in an examination report 2 associated with the image data set 1 and written in natural language.

The method uses these examination results, namely the image data set 1 and its associated examination report 2, to generate structured information describing medical concepts relevant to the patient in a result data structure 3. The result data structure 3 refers to a medical ontology comprising hierarchically structured medical concepts, wherein, in the result data structure, detected medical concepts are marked by binarily activating them.

Figure 2:
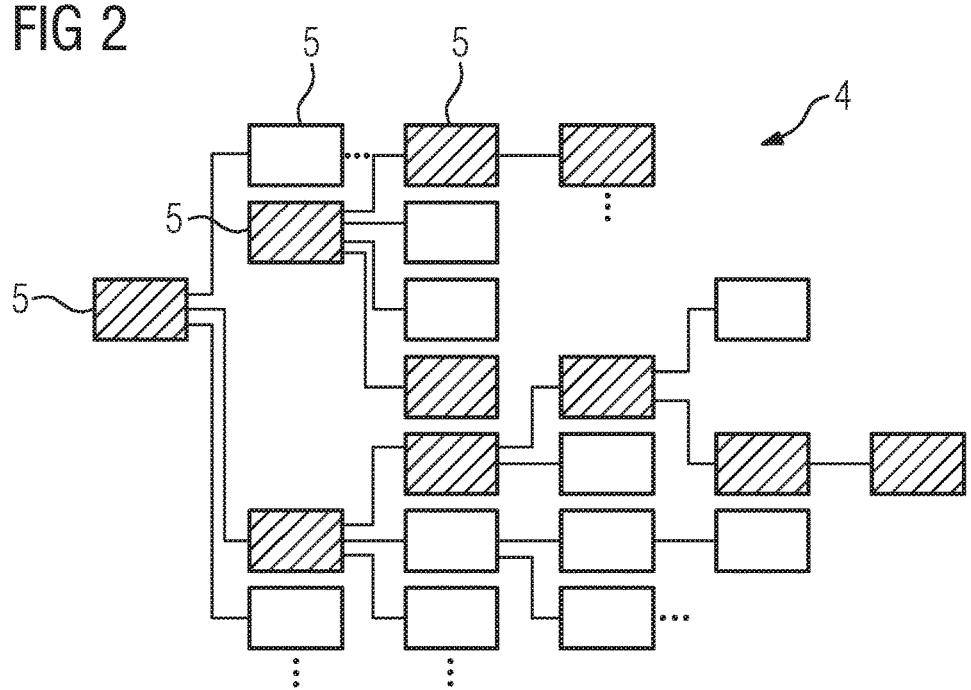
FIG. 2 illustrates the hierarchical structure of a medical ontology.

The hierarchical structure of the medical ontology 4 is visualized by FIG. 2, showing an excerpt of the medical concepts 5 of the medical ontology 4. The medical ontology 4 may be based on at least one predefined known ontology and/or denotation standard (lexicon), which may, for example, cover certain sections/trees of the medical ontology 4. On the other hand, mapping functions are provided which map medical concepts 5 of the medical ontology 4, activated or marked in a result data structure 3, to predefined known ontologies and/or denotation standards (lexicons), so that evaluation applications 6 to be discussed later may use the most expedient context to work in.

In preferably parallelly executed steps S1, S2, respective first and second analysis algorithms are used to analyse the image data set 1 and the examination report 2 for detection of medical concepts 5 of the medical ontology 4. Detected medical concepts 5 are marked in the result data structure 3, in particular binary.

In step S1, at least one first analysis algorithm, which comprises at least one convolutional neural network and thus is an artificial intelligence algorithm, is used to detect the presence of medical concepts 5 in the image data set 1. In this respect, CNN detectors may be used as or as part of first analysis algorithms to detect single medical concepts 5 and/or groups of medical concepts 5, for example in the hierarchical level of one tree of the medical ontology 4. This has multiple advantages, since CNN detectors only have to be run if certain hierarchically higher medical concepts 5 have been detected before, in particular superordinate medical concepts 5. Additionally, certain detections may be left out if the associated medical concepts 5 are not relevant for the evaluation applications used, conferring flexibility. Further, when training the first analysis algorithm, training results for a superordinate medical concept 5 may be used to initiate training for subordinate medical concepts 5.

Training data sets may comprise training image data sets, and results of medical concept detection by using a second analysis algorithm on an associated training examination report and/or manual annotations as ground truth. Training image data sets for which a medical concept 5 has been marked/activated are used as positive examples regarding this concept 5, those in which the medical concept 5 has not been marked as negative examples.

In step S2, the at least one second analysis algorithm is used to detect the presence of medical concepts 5 in the radiological examination report 2 by natural language processing (NLP), as, for example, described in Ewoud Pons et al., "Natural Language Processing in Radiology: A Systematic Review", Radiology 279:329-343 (2016), the entire contents of which are incorporated herein by reference. Again, different second analysis algorithms/detectors may be applied for different medical concepts 5 and/or groups of medical concepts 5, as discussed with respect to the first analysis algorithm. Second analysis algorithms may be rule-based and/or machine learning-based, depending on the medical concept 5 and its complexity.

In both steps S1 and S2, the detected concepts are marked within the result data structure 3, leading to an aggregation of the results. However, in an optional step S3, a comparison of the detection results may be performed. If, in this comparison, it is observed that a relevant medical concept 5 from a predetermined relevancy group has been detected in the image data set 1, but not in the associated examination report 2, a notification leading to re-assessment of the image data set 1, for example an extra viewing regarding the medical concept 5, may be output or other measures may be triggered.

In the example of FIG. 2, marked medical concepts 5 are shown shaded; these may for example comprise "Chest Imaging", "Pneumothorax"/"Lung Nodules" in one hierarchic tree, "Cardiac Imaging", "Valvular Disease", "Aortic Valve", "Aortic Stenosis" and "Aortic Valve Calcification" in another tree. As can be seen, at least some hierarchical levels are structured according to anatomical features. Other examples for medical concepts 5 may comprise "Neuro Imaging", "Left Ventricular Enhancement", "Lung Cancer" and the like.

In any case, the result data structure 3 is then provided to evaluation applications 6, comprising, for example, an interpretation assistance application, a billing/coding application, a legal assessment application, a clinical trial application, a clinical management application, a radiological report assistance application and the like.

In an especially preferred interactive mode, analysis takes place while the radiological examination report 3 is drafted. In this case, proposals for phrasing and the like may be provided and hints on medical concepts and their denotation can be output. Auto-filling functions may be added. Multi-language support and formulation suggestions regarding standards/lexica or classifications can also be provided. Similar cases may be retrieved by comparing marked medical concept patterns, in particular weighing some medical concepts 5 accordingly. Alerts may be propagated in the computer system in which the method is performed when critical medical concepts 5, i.e. describing critical findings, occur which lead to a different handling of the patient. Pertinent evaluation algorithms 6 for these features comprise radiological report assistance applications, related cases finding assistants and propagation applications.

Of course, other evaluation applications 6 may also be used on a current result data structure 3 or multiple result data structures 3 for different patients stored in a database. Their functions not only comprise post-processing of examination reports 2, but also automated billing and coding, cohort generation and the like.

Figure 3:
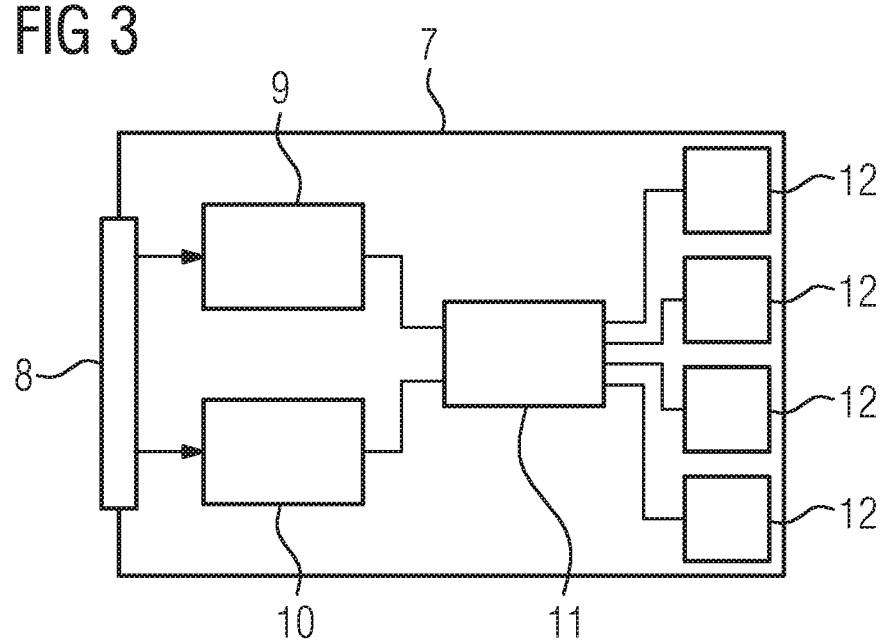
FIG. 3 is a functional view of an evaluation system according to an embodiment of the invention.

FIG. 3 shows the functional structure of an evaluation system 7 according to an embodiment of the invention, thus adapted to perform the inventive method by using at least one computing device/computer. The evaluation system 7 comprises an interface 8 for receiving examination results and a number of subsystems, namely a first concept detection unit 9 for extraction of structured information from image data sets 1, a second concept detection unit 10 for extraction of structured information from text, i.e. the examination reports 2, an output unit 11 for data representation in form of the result data structure 3 relating to the medical ontology 4, and multiple application units 12 for specific evaluation applications 6. Of course, determined result data structures 3 may also be stored in a database for other evaluation applications 6 and/or those applied later.

Figure 4:
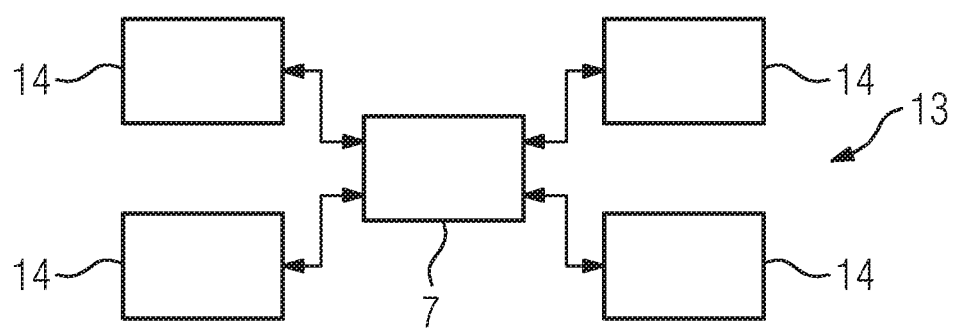
FIG. 4 shows the evaluation system embedded into a computer system.

FIG. 4 shows a principle drawing of a computer system 13 of a medical facility. The computer system 13 comprises an evaluation system 7 as described above, as well as further systems 14 to which critical findings can be propagated, for example information systems (HIS/RIS), image acquisition devices, viewing stations, etc.

Although the present invention has been described in detail with reference to the example embodiments, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for evaluating medical examination results of a patient based on a medical ontology, the medical examination results including at least one image data set of the patient and at least one examination report written in natural language, the medical ontology including multiple medical concepts, and the method, performed using a computing device, comprising:
   analysing the at least one image data set using at least one first analysis algorithm, the at least one first analysis algorithm being an artificial intelligence algorithm, the analysing the at least one image data set including
      detecting first medical concepts of the medical ontology, and
      marking detected ones of the first medical concepts in a result data structure referring to the medical ontology;
   analysing the at least one examination report using at least one second analysis algorithm, the at least one second analysis algorithm being a natural language processing algorithm, the analysing the at least one examination report including
      detecting second medical concepts of the medical ontology, and
      marking detected ones of the second medical concepts in the result data structure; and
   providing the result data structure to at least one evaluation application.

2. The method of claim 1, wherein
   the medical ontology has a hierarchical structure,
   at least one of (i) the at least one first analysis algorithm includes multiple first analysis algorithms or (ii) the at least one second analysis algorithm includes multiple second analysis algorithms,
   the analysing the at least one image data set includes using the multiple first analysis algorithm following the hierarchical structure, and
   the analysing the at least one examination report includes using the multiple second analysis algorithms following the hierarchical structure.

3. The method of claim 2, wherein the medical ontology is based on at least one of (i) at least one defined ontology or (ii) at least one defined denotation standard, and the method further comprises:
   mapping the medical ontology to the at least one (i) the at least one defined ontology or (ii) at least one defined denotation standard.

4. The method of claim 2, wherein the at least one first analysis algorithm corresponds with at least one of single medical concepts or groups of medical concepts of hierarchically structured medical ontology, and the method further includes at least one of,
   training the at least one first analysis algorithm for a hierarchically relatively lower medical concept based on training results for a hierarchically next relatively higher medical concept, or
   determining training data sets by applying the at least one second analysis algorithm to a training examination report associated with a training image data set, and forming a ground truth for the training image data set based on results of the applying the at least one second analysis algorithm.

5. The method of claim 2, wherein the analysing the examination report includes
   extracting features, and
   detecting the second medical concepts based on the extracted features.

6. The method of claim 2, wherein at least one of the at least one second analysis algorithm is at least one of at least partly rule-based or at least partly artificial intelligence-based.

7. The method of claim 1, wherein the medical ontology is based on at least one of (i) at least one defined ontology or (ii) at least one defined denotation standard, and the method further comprises:
   mapping the medical ontology to the at least one of (i) the at least one defined ontology or (ii) the at least one defined denotation standard.

8. The method of claim 1, wherein the at least one first analysis algorithm includes a convolutional neural network.

9. The method of claim 8, wherein the method further comprises:
   training the convolutional neural network using deep learning techniques.

10. The method of claim 1, wherein the at least one first analysis algorithm corresponds with at least one of single medical concepts or groups of medical concepts of hierarchically structured medical ontology, and the method further includes at least one of,
    training the at least one first analysis algorithm for a hierarchically relatively lower medical concept based on training results for a hierarchically next relatively higher medical concept, or
    determining training data sets by applying the at least one second analysis algorithm to a training examination report associated with a training image data set, and forming a ground truth for the training image data set based on results of the applying the at least one second analysis algorithm.

11. The method of claim 1, wherein the analysing the examination report includes
    extracting features, and
    detecting the second medical concepts based on the extracted features.

12. The method of claim 1, wherein at least one of the at least one second analysis algorithm is at least one of at least partly rule-based or at least partly artificial intelligence-based.

13. The method of claim 1, further comprising:
    comparing the first medical concepts and the second medical concepts; and
    outputting a notification, in response to the comparing indicating that at least one medical concept included in the first medical concepts is not included in the second medical concepts.

14. The method of claim 1, further comprising:
selecting the at least one evaluation application from among
an interpretation assistance application,
at least one of a billing application, a coding application, a quality assessment application or a legal assessment application,
at least one of a clinical trial application or a clinical management application, and
a radiological report assistance application.

15. The method of claim 14, wherein the interpretation assistance application is at least one of
a propagation application configured to propogate critical findings through rule based evaluation of the result data structure, or
a related cases finding application configured for comparing a result data structure of a current patient with result data structures of other patients stored in a database.

16. The method of claim 14, wherein at least one of
the clinical trial application is configured to retrieve cases corresponding with a requirement definition for at least one of a prospective study or a historical study based on the result data structure, or
the clinical management application is configured to generate recommendations on further procedures regarding the patient based on the result data structure and clinical guidelines.

17. The method of claim 14, wherein the radiological report assistance application is configured to at least one of
generate drafts for examination reports based on the image data set and result data structures of at least one previous examination result, or
perform at least one of real time assistance or post-processing assistance based on the result data structures.

18. A non-transitory computer program product, storing a computer program to perform the method of claim 1 when executed on a computing device.

19. A non-transitory electronically readable storage medium storing a computer program to perform the method of claim 1 when executed on a computing device.

20. An evaluation system for evaluating medical examination results of a patient based on a medical ontology, the medical examination results including at least one image data set of the patient and at least one examination report written in natural language, the medical ontology including multiple medical concepts, and the evaluation system comprising:
at least one processor configured to
analyse the at least one image data set using at least one first analysis algorithm, the at least one first analysis algorithm being an artificial intelligence algorithm configured to
detect first medical concepts of the medical ontology, and
mark detected ones of the first medical concepts in a result data structure referring to the medical ontology,
analyse the at least one examination report using at least one second analysis algorithm, the at least one second analysis algorithm being a natural language processing algorithm configured to
detect second medical concepts of the medical ontology, and
marking detected ones of the second medical concepts in the result data structure, and
provide the result data structure to at least one evaluation application.

* * * * *